US010952434B2

(12) United States Patent
Chauhan

(10) Patent No.: US 10,952,434 B2
(45) Date of Patent: Mar. 23, 2021

(54) COMPOSITIONS AND METHODS FOR ATTRACTING INSECTS

(71) Applicant: The United States of America, as Represented by the Secretary of Agriculture, Washington, DC (US)

(72) Inventor: Kamlesh R. Chauhan, Laurel, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 114 days.

(21) Appl. No.: 15/856,280

(22) Filed: Dec. 28, 2017

(65) Prior Publication Data

US 2018/0184653 A1 Jul. 5, 2018

Related U.S. Application Data

(60) Provisional application No. 62/440,518, filed on Dec. 30, 2016.

(51) Int. Cl.
*A01N 43/08* (2006.01)
*A01N 43/28* (2006.01)
*A01N 43/30* (2006.01)
*A01N 35/02* (2006.01)
*A01N 31/06* (2006.01)
(Continued)

(52) U.S. Cl.
CPC ............. *A01N 43/28* (2013.01); *A01N 31/06* (2013.01); *A01N 35/02* (2013.01); *A01N 43/08* (2013.01); *A01N 43/30* (2013.01); *C07C 43/184* (2013.01); *C07C 43/317* (2013.01); *C07D 307/20* (2013.01); *C07D 317/12* (2013.01);
(Continued)

(58) Field of Classification Search
None
See application file for complete search history.

(56) References Cited

U.S. PATENT DOCUMENTS

2008/0013042 A1* 1/2008 Habassi ............... C08F 220/26
351/159.01
2015/0164764 A1* 6/2015 Bonnet ................. A61K 8/602
514/777

FOREIGN PATENT DOCUMENTS

JP H05230048 A 9/1993
WO 2007030963 A1 3/2007

OTHER PUBLICATIONS

Csóka M, Amtmann M, Sárdy DN, Kállay M, Korány K. GC-MS description of the primary aroma structure of two Kadarka wines considered indigenous in Hungary. Journal of Applied Botany and Food Quality. Sep. 24, 2013;86(1). (Year: 2013).*

(Continued)

*Primary Examiner* — Nissa M Westerberg
(74) *Attorney, Agent, or Firm* — G. Byron Stover; John Fado

(57) ABSTRACT

Disclosed are compositions for attracting insects (e.g., harmful or troublesome insects such as blood-sucking and biting insects, ticks and mites) to an object (e.g., insect trap) or area (e.g., field, orchard). Also disclosed are methods for attracting insects involving treating (or exposing) the object or area with a composition containing compounds described herein (e.g., a pro-fragrance compound selected from the group consisting of an acetal, a ketal, hemiacetal and mixtures thereof, wherein at least one of a parent aldehyde, ketone, or alcohol of the pro-fragrance acetal or ketal is a fragrance compound), and optionally a carrier or carrier material.

2 Claims, 2 Drawing Sheets

1

2

3   4   5

(51) Int. Cl.
*C07D 317/72* (2006.01)
*C07C 43/184* (2006.01)
*C07D 307/20* (2006.01)
*C07D 317/12* (2006.01)
*C07C 43/317* (2006.01)

(52) U.S. Cl.
CPC ........ *C07D 317/72* (2013.01); *C07C 2601/08* (2017.05); *C07C 2601/14* (2017.05)

(56) References Cited

OTHER PUBLICATIONS

Liu, X. et al., Propheromones That Release Pheromonal Carbonyl Compounds in Light, Journal of Chemical Ecology, (1984) 10(5):809-822.
Buttner, Matthias W. et al., Disila-Okoumal: A Silicon Analogue of the Ambergris Odorant Okoumal, ChemBioChem, (2007), 8:1447-1454.
International Searching Authority, PCT/US2017/068886 for The United States of America, as Represented by the Secretary of Agriculture, International Filing Date Dec. 29, 2017, AG011815-+PCT.

\* cited by examiner

Cyclopentanone

Cyclohexanone

I-152

I-90

I-95

I-182

I-96

COMPOSITIONS AND METHODS FOR ATTRACTING INSECTS

REFERENCE TO RELATED APPLICATION

This application claims the benefit of U.S. Provisional Application No. 62/440,518 filed 30 Dec. 2016, which is incorporated herein by reference in its entirety.

BACKGROUND OF THE INVENTION

Disclosed are compositions for attracting insects (e.g., harmful or troublesome insects such as blood-sucking and biting insects, ticks and mites). Also disclosed are methods for attracting insects to an object (e.g., insect trap) or area (e.g., field, orchard), involving treating (or exposing) the object or area with a composition containing compounds described herein (e.g., a pro-fragrance compound selected from the group consisting of an acetal, a ketal, hemiacetal and mixtures thereof, wherein at least one of a parent aldehyde, ketone, or alcohol of the pro-fragrance acetal or ketal is a fragrance compound), and optionally a carrier or carrier material.

The growing trend towards urban migration in the developing world has led to frequent outbreaks of vector borne diseases like Dengue fever, Yellow fever, and Chikungunya transmitted by, *Aedes aegypti*, a container breeding species of mosquito. A major portion of vector control strategies involves the use of either adulticides or larvicides. However, there are growing concerns about the shortcomings of such routinely applied control measures.

Arthropod vectors (e.g., mosquitos) show robust semiochemicals induced behaviors. Volatile organic compounds are used as major cues for tracking and surveillance of insect pest and arthropod vectors alike. These chemicals elicit behaviors such as attraction or repulsion/avoidance while vectors seek habitats, hosts, mates, or oviposition sites. Olfactory structures and function in arthropod vectors lead to identification and use of chemical ligands (Zain, S., Current Opinion in Insect science, 10: 83-89 (2015)). These chemical stimuli can be used for monitoring; however, they cannot be used to make commercially-viable products because of lack of stability and high volatility.

Mosquitoes of all species use chemical cues to find their hosts in nature. Carbon dioxide ($CO_2$) is widely recognized as one of the strongest attractants for adult mosquitoes, particularly blood-seeking females. For this reason, $CO_2$ is the main chemical attractant in traps targeting adult mosquitoes for control and surveillance. However, the deployment of $CO_2$ in the field is often logistically difficult and expensive as it normally requires the purchase and mobilization of blocks of dry ice, compressed gas cylinders, regulating nozzles, etc. Other commercially available lures utilize a range of chemical compounds to attract mosquitoes, although their effectiveness is generally inferior in comparison to $CO_2$. This situation strongly limits the practicality of current trapping methods, especially in rural and/or underdeveloped areas where they are often needed most.

Recently, cyclopentanone (an organic ketone commonly used as a flavoring/odorant agent, categorized by the US Food and Drug Administration as "Generally Regarded as Safe") was reported to mimic the attractive effect of $CO_2$ in mosquitoes by stimulating the olfactory receptors normally responsible for the perception of $CO_2$ (Tauxe, G. M., et al., Cell, 155(6): 1365-1379 (2013); Choo, Y-M., Xu, P., Hwang, J. K., Zeng, F., Tan, K., Bhagavathy, G., Chauhan K. R., and Leal W. S., 2017, Reverse chemical ecology approach for the identification of a mosquito oviposition attractant, Proceeding of National Academy of Science (in press)). In semi-field trials, the attractiveness of traps baited with cyclopentanone was equivalent to that of matching control traps baited with $CO_2$. However, cyclopentanone poses one challenge for its deployment in the field: due to its high volatility, cyclopentanone evaporates extremely fast, thus making it hard to achieve the homogeneous, slow-release effect required for effective mosquito trapping.

There thus exists a need for other chemicals in order to attract pests such as mosquitoes.

SUMMARY OF THE INVENTION

Disclosed are compositions for attracting insects (e.g., harmful or troublesome insects such as blood-sucking and biting insects, ticks and mites). Also disclosed are methods for attracting insects to an object (e.g., insect trap) or area (e.g., field, orchard), involving treating (or exposing) the object or area with a composition containing compounds described herein (e.g., a pro-fragrance compound selected from the group consisting of an acetal, a ketal, hemiacetal and mixtures thereof, wherein at least one of a parent aldehyde, ketone, or alcohol of the pro-fragrance acetal or ketal is a fragrance compound; for example, see FIG. 1 and FIG. 2), and optionally a carrier or carrier material.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Figure 1:
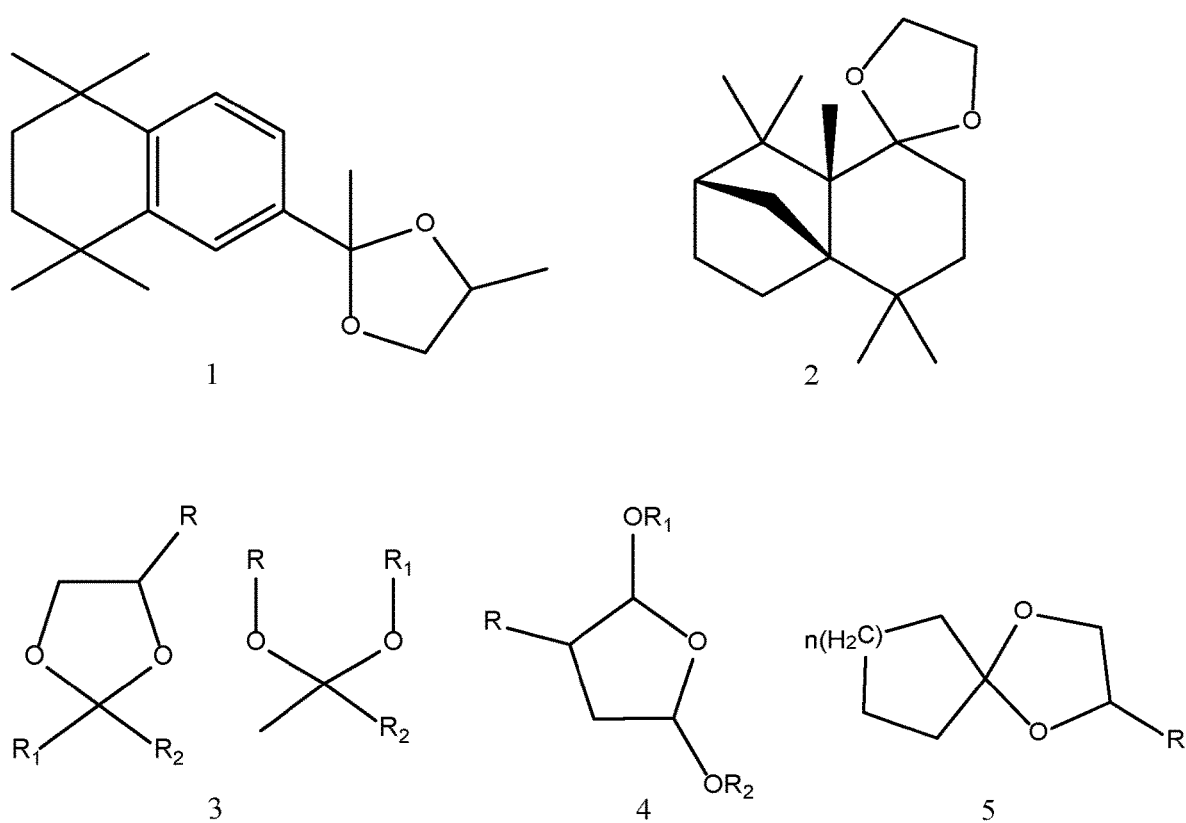
FIG. 1 shows the chemical structures of two candidate attractants (1, 2) and general scaffolds (3, 4, 5,) where, for example, R, $R_1$, $R_2$: H, n-alkanes, alkanes, cycloalkanes, aryl and n: 1 to 8 as described below.

Disclosed are compositions for attracting insects (e.g., harmful or troublesome insects such as blood-sucking and biting insects, ticks and mites). Also disclosed are methods for attracting insects to an object (e.g., insect trap) or area (e.g., field, orchard), involving treating (or exposing) the object or area with a composition containing compounds described herein (e.g., a pro-fragrance compound selected from the group consisting of an acetal, a ketal, hemiacetal and mixtures thereof, wherein at least one of a parent aldehyde, ketone, or alcohol of the pro-fragrance acetal or ketal is a fragrance compound), and optionally a carrier or carrier material. The term "insects" as used herein includes non-insects such as ticks, mites, spiders, centipedes, scorpions, chiggers, and solifugids.

The present research is directed to a pro-fragrance compound selected from the group consisting of an acetal, a ketal, hemiacetal and mixtures thereof, wherein at least one of a parent aldehyde, ketone, or alcohol of the pro-fragrance acetal or ketal is a fragrance compound, having less volatility compared to monoterpenes. Instead of focusing on slow release of highly volatile compounds, the research focused on structure activity of related acetals and ketals as insect (e.g., mosquito) attractant and feeding stimulants to be utilized as attract and kill baits. A core structure containing acetals and ketals of oxygenated sesquiterpenes (C15) was discovered to attract blood feeding mosquitoes in wind tunnel experiments. In in vitro bioassays, six analogs based on this core structural feature showed promising attraction/arresting (or feeding stimulant) effects compared to cyclopentanone against biting insects. The laboratory studies consistently showed that these compounds exhibited consistent feeding and spatial attraction to adult mosquitoes at variable doses. Such newly discovered attractants would be ideal candidates as mosquito baits as well as other vectors of diseases, such as ticks, sandflies, and stable flies responding to $CO_2$ as feeding cue.

Disclosed are insect attracting compositions containing at least one compound of:

formula 1

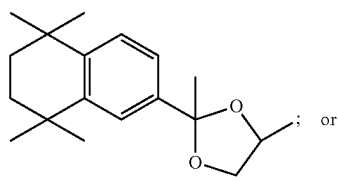

1 ; or formula 2

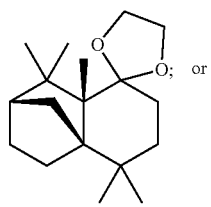

2 ; or formula 3

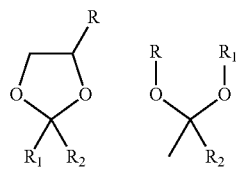

3 where R, $R_1$, and $R_2$ are H, n-alkanes, alkanes, cycloalkanes, or aryl; where n-alkanes are $(CH_2)_nH$ where n is 1 to 8 (preferably 2 to 4), alkanes are branched-$(CH_2)_nH$ where n is 1 to 8 (preferably 2 to 4); cycloalkanes are cyclobutane, cyclopentane, cyclohexane, or cycloheptane, aryl is benzene or alkyl benzene (C1-6 alkyl, preferably C1-4 such as methyl, ethyl, n-propyl, isopropyl); or formula 4

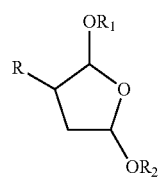

4 where R, $R_1$, and $R_2$ are H, n-alkanes, alkanes, cycloalkanes, or aryl; n-alkanes are —$(CH_2)_nH$ where n is 1 to 8 (preferably 2 to 4), alkanes are branched-$(CH_2)_nH$ where n is 1 to 8 (preferably 2 to 4); cycloalkanes are cyclobutane, cyclopentane, cyclohexane, or cycloheptane, aryl is benzene and or alkyl benzene (C1-6 alkyl, preferably C1-4 such as methyl, ethyl, n-propyl, isopropyl); or formula 5

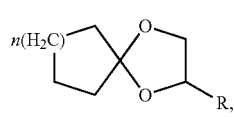

5 where R is H, n-alkanes, alkanes, cycloalkanes, or aryl and n: 1 to 8 (preferably 2 to 4); n-alkanes are —$(CH_2)_nH$ where n is 1 to 8 (preferably 2 to 4), alkanes are branched-$(CH_2)_nH$ where n is 1 to 8 (preferably 2 to 4); cycloalkanes are cyclobutane, cyclopentane, cyclohexane, or cycloheptane, aryl is benzene or alkyl benzene (C1-6 alkyl, preferably C1-4 such as methyl, ethyl, n-propyl, isopropyl);

and optionally a carrier or carrier material;

or wherein the composition contains at least two compounds of formulae 1, 2, 3, 4 and/or 5 (for example, the composition contains a compound of formula 1 and a compound of formula 2, a compound of formula 3 and a compound of formula 4, a compound of formula 1 and a compound of formula 5, two compounds of formula 3, etc.; in other words, any combination of 2 compounds) or wherein the composition contains at least three compounds of formulae 1, 2, 3, 4 and/or 5 (for example, the composition contains a compound of formula 1 and a compound of formula 2 and a compound of formula 4, a compound of formula 3 and a compound of formula 4 and a compound of formula 1, two compounds of formula 3 and 1 compound of formula 2, three compounds of formula 3, etc.; in other words, any combination of 3 compounds) or wherein the composition contains at least four compounds of formulae 1, 2, 3, 4 and/or 5 (for example, the composition contains a compound of formula 1 and a compound of formula 2 and a compound of formula 3 and a compound of formula 4, or a compound of formula 2 and a compound of formula 3 and a compound of formula 4 and a compound of formula 5, 2 compounds of formula 4 and a compound of formula 2 and a compound of formula 3, 3 compounds of formula 3 and a compound of formula 4, 2 compounds of formula 4 and 2 compound of formula 3, 4 compounds of formula 5, etc.; in other words, any combination of 4 compounds) or wherein the composition contains at least five compounds of formulae 1, 2, 3, 4 and 5 (for example, the composition contains a compound of formula 1 and a compound of formula 2 and a compound of formula 3 and a compound of formula 4 and a compound of formula 5, or 2 compounds of formula 4 and 1 compound of formula 2 and 1 compound of formula 3 and 1 compound of formula 5, or 2 compounds of formula 5 and 2 compounds of formula 3 and 1 compound of formula 4, etc.; in other words, any combination of 5 compounds).

Also disclosed are methods for attracting insects (e.g., harmful or troublesome insects such as blood-sucking and biting insects, ticks and mites) to an object (e.g., insect trap) or area (e.g., field, orchard), involving treating (or exposing) the object or area with a composition containing at least one compound of:

formula 1

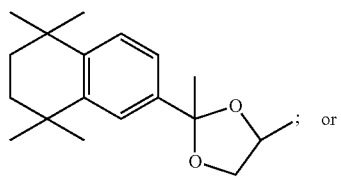

formula 2

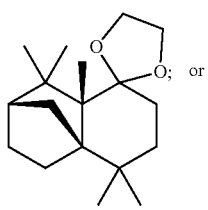

formula 3

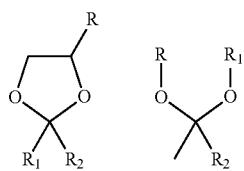

where R, $R_1$, and $R_2$ are H, n-alkanes, alkanes, cycloalkanes, or aryl; where n-alkanes are $(CH_2)_n H$ where n is 1 to 8 (preferably 2 to 4), alkanes are branched-$(CH_2)_n H$ where n is 1 to 8 (preferably 2 to 4); cycloalkanes are cyclobutane, cyclopentane, cyclohexane, or cycloheptane, aryl is benzene or alkyl benzene (C1-6 alkyl, preferably C1-4 such as methyl, ethyl, n-propyl, isopropyl);

or formula 4

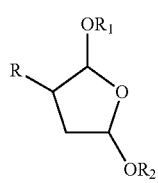

where R, $R_1$, and $R_2$ are H, n-alkanes, alkanes, cycloalkanes, or aryl; n-alkanes are —$(CH_2)_n H$ where n is 1 to 8 (preferably 2 to 4), alkanes are branched-$(CH_2)_n H$ where n is 1 to 8 (preferably 2 to 4); cycloalkanes are cyclobutane, cyclopentane, cyclohexane, or cycloheptane, aryl is benzene or alkyl benzene (C1-6 alkyl, preferably C1-4 such as methyl, ethyl, n-propyl, isopropyl); or formula 5

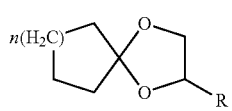

where R is H, n-alkanes, alkanes, cycloalkanes, or aryl and n: 1 to 8 (preferably 2 to 4); n-alkanes are —$(CH_2)_n H$ where n is 1 to 8 (preferably 2 to 4), alkanes are branched-$(CH_2)_n H$ where n is 1 to 8 (preferably 2 to 4); cycloal-kanes are cyclobutane, cyclopentane, cyclohexane, or cycloheptane, aryl is benzene or alkyl benzene (C1-6 alkyl, preferably C1-4 such as methyl, ethyl, n-propyl, isopropyl);

and optionally a carrier or carrier material;

or wherein the composition contains at least two compounds of formulae 1, 2, 3, 4 and/or 5 (for example, the composition contains a compound of formula 1 and a compound of formula 2, a compound of formula 3 and a compound of formula 4, a compound of formula 1 and a compound of formula 5, two compounds of formula 3, etc.; in other words, any combination of 2 compounds) or wherein the composition contains at least three compounds of formulae 1, 2, 3, 4 and/or 5 (for example, the composition contains a compound of formula 1 and a compound of formula 2 and a compound of formula 4, a compound of formula 3 and a compound of formula 4 and a compound of formula 1, two compounds of formula 3 and 1 compound of formula 2, three compounds of formula 3, etc.; in other words, any combination of 3 compounds) or wherein the composition contains at least four compounds of formulae 1, 2, 3, 4 and/or 5 (for example, the composition contains a compound of formula 1 and a compound of formula 2 and a compound of formula 3 and a compound of formula 4, or a compound of formula 2 and a compound of formula 3 and a compound of formula 4 and a compound of formula 5, 2 compounds of formula 4 and a compound of formula 2 and a compound of formula 3, 3 compounds of formula 3 and a compound of formula 4, 2 compounds of formula 4 and 2 compound of formula 3, 4 compounds of formula 5, etc.; in other words, any combination of 4 compounds) or wherein the composition contains at least five compounds of formulae 1, 2, 3, 4 and 5 (for example, the composition contains a compound of formula 1 and a compound of formula 2 and a compound of formula 3 and a compound of formula 4 and a compound of formula 5, or 2 compounds of formula 4 and 1 compound of formula 2 and 1 compound of formula 3 and 1 compound of formula 5, or 2 compounds of formula 5 and 2 compounds of formula 3 and 1 compound of formula 4, etc.; in other words, any combination of 5 compounds).

The compositions can therefore be used for attracting insects such as harmful or troublesome blood-sucking, stinging and biting insects, ticks and mites. The term "insects" as used herein includes non-insects such as ticks, mites, spiders, centipedes, scorpions, chiggers, and solifugids.

The blood-sucking insects include mosquitoes (for example *Aedes, Culex* and *Anopheles* species including but not limited to Tiger mosquitoes, *Aedes aboriginis, Aedes aegypti, Aedes albopictus, Aedes cantator, Aedes sierrensis, Aedes sollicitans, Aedes squamiger, Aedes sticticus*), sand flies (for example *Phlebotomus* and *Lutzomyia* species), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), black flies (*Prosimuliim mixtum, Cnephia pecuarum, Simuliim vittatum*), flies which cause myiasis (for example *Lucilia cuprina, Chrysomyia chlorpyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example

*Melaphagus orinus*), fleas (for example *Pulex irritans, Cthenocephalides canis* and *Xenopsylla cheopis*) and sand fleas (for example *Dermatophilus penetrans*).

The biting insects include cockroaches (for example *Blattella germanica, Periplaneta americana, Blatta orientalis* and *Supella supellectilium*), beetles (for example *Sitophilus granarius, Tenebrio molitor, Dermestes lardarius, Stegobium paniceum, Anobium puntactum* and *Hylotrupes bajulus*), termites (for example *Reticulitermes lucifugus*) and ants (for example *Lasius niger*).

The ticks include, for example, *Ornithodorus moubata, Ixodes ricinus, I. scapularis, Boophilus microplus, Dermacentor variabilis, D. andersoni, Hyalomma marginatum, H. anatolicum, Amblyomma hebreum*, and *A. americanum*, and mites include, for example, *Sarcoptes scabiei* and *Dermanyssus gallinae*.

Spiders include, for example, *Lactrodectus mactans, Loxosceles recluse, Tegenaria agrestis (Walckenaer), Achaearanea tepidariorum, Salticidae, Pholcus phalangioides*, and *Lycosa*.

Centipede include, *Scutigera coleoptrata*.

Scorpions include, for example, *Centruroides exilicauda, Centruroides vittatus, Hadrurus arizonensis*, and *Solifugae*.

Solifugids include, for example, *Solifugae*.

The composition containing the compounds described herein optionally contains a carrier (e.g., agronomically or physiologically or pharmaceutically acceptable carrier). The methods include dispensing the compounds described herein into the environment in vapor form (e.g., an aerosol) preferably using devices (e.g., passive eminators) that allow a slow sustained release of these compounds into the environment. Attractant components can be absorbed on to delignified wood chips so that sustained release of the vapors can be maintained at desired concentration and time. The carrier component can be a liquid or a solid material. The term "carrier" as used herein includes carrier materials such as those described below. As is known in the art, the vehicle or carrier to be used refers to a substrate such as a mineral oil, paraffin, silicon oil, water, membrane, sachets, disks, rope, vials, tubes, septa, resin, hollow fiber, microcapsule, cigarette filter, gel, natural and/or synthetic polymers, elastomers or the like. All of these substrates have been used to control and release an effective amount of a composition containing the compounds disclosed herein in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, laminates, cellulosic and rubber matrices and synthetic polymer matrices, or the like.

The terms "object" or "area" as used herein include any place, including any type of premises, which can be out-of-doors, such as in farms, orchards, parks, yards, gardens, lawns, tents, camping bed nets, camping areas, forests, and so forth, or indoors, such as in barns, garages, commercial buildings, homes, silos, grain storage, and so forth, or any area where pests are a problem, such as in shipping or storage containers (e.g., luggage, bags, boxes, crates, etc.), packing materials, bedding, and so forth; also includes clothing.

The amount of attractant used will be at least an effective amount. The term "effective amount," as used herein, means the minimum amount of attractant needed to attract, for example, mosquitoes to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% of mosquitoes and would be statistically significant in comparison to a control.

Other compounds (e.g., insect attractants known in the art) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising an insecticide" means that the composition may or may not contain an insecticide and that this description includes compositions that contain an insecticide and do not contain an insecticide.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Mosquitoes: *Aedes aegypti* (Liverpool) were reared in an insectary using standard rearing procedures. Approximately 50 larvae were reared in plastic cups (13×7×7.5 cm) at 27±1° C., and were fed ground up fish pellets. Adults were contained in plastic cartons covered by nylon screening and were fed using cotton pads soaked in a 10% glucose solution. Prior to blood feeding, 20 adult females, approximately 6 to 8 days old, were aspirated out of the rearing cartons and placed in to a stock cage (20×20×20 cm).

Test compounds and exposure concentrations: The compounds used in the tests were acetals, hemiacetals and ketals of oxygenated sesquiterpenes and substituted ketones, aldehydes, cyclopentanone, cyclohexanone, and ketals. The chemical purity of all chemicals were determined by capillary gas-liquid chromatography (~98% chemical purity) and neat compounds at the concentration of 5 to 50 µg/ml were tested. All bioassays were conducted in the hood and wind tunnel at the USDA Beltsville Agriculture Research Center.

Highthrouhput Feeding Assay: The K&D module was developed at USDA for evaluating feeding deterrence and toxicity of candidate topical repellents against hemophagus arthropod vectors (Klun, J. A., and M. Debboun, J. Med. Entomol., 37: 177-181 (2000)). In the present study the K&D module was used as a highthrouhput screening tool to evaluate response of *Ae. aegypti* to attractant\feeding stimuli.

Consistent response of selected compounds exhibited significant feeding stimuli in the K&D module, in the wind tunnel bioassay, and in the attract and kill bait formulations. In vitro bioassays were conducted as described by Klun et. al., 2000. Each test replicate consisted of three treatments: a control (EtOH); a standard (Deet, 4.54 nmol/µl); and an experimental compound (feeding attractants, 4.54 nmol/µl). The three treatments were randomly assigned to consecutive cells in 2,6-cell reservoirs connected in series to a single water-bath pump; thus, 4 replicates could be tested/run.

Tests were performed in an Air Science USA hood, with an air movement velocity of approx. 110-120 ft./min., temperature of 25-27° C., and RH of 15-25%. A six-celled reservoir was connected to and heated by a constant-temperature (38° C.) water circulator (Lauda E100, Wobser GMGH and Co., Konigshofell, Germany).

Prior to each test, the upper surface of each reservoir was coated with a thin layer of high-vacuum silicone grease (Dow Corning Corp., Midland, Mich.), and the cells then filled (approx. 6 ml. capacity) or topped-off with the following: (1) expired human red blood cells suspended in citrate-phosphate-dextrose-adenine (CPDA) solution, not more than 1 month past expiration date, and to which 110 mg ATP/35 ml. blood-CPDA had been added on the day of testing; or (2) CPDA+ATP×$10^{-3}$, usually made up or diluted to $10^{-3}$ ATP on the day of testing.

The filled cells were then covered with an Edicol collagen membrane strip (Devro, Sandy Run, S.C.), and then with a just-treated (110 µl of 4.54 nmol/µl treatment or control solution) organdy cloth strip (G Street Fabrics, Rockville, Md.).

Mosquitoes used in the tests were either *Aedes aegypti* (Liverpool) or *Aedes albopictus* (Asian Tiger mosquitoes (ATMs)). *Ae. aegypti* and *Ae. albopictus* were originally obtained from colonies at the Walter Reed Army Institute of Research (WRAIR), Silver Spring, Md., and were maintained in colonies at the Beltsville Agricultural Research Center, USDA, ARS, Beltsville, Md. The larvae were reared (Gerber, E. J., et al., Manual for mosquito rearing and experimental techniques, Am. Mosq. Control Assoc. Bull. 5 (revised), AMCA, Inc., Lake Charles, La. (1994)) by feeding larvae ground tropical fish pellets (Hikari Cichlid Gold Fish Food, Kamihata Fish Ind. Ltd., Himeji, Japan, www.hikari-.info). Adults were held at 12:12 h (light:dark) photoperiod at 26° C. and 50% RH, and fed with a cotton pad moistened with 10% aqueous sucrose solution. For both species, adult mosquitoes used in the tests were between 5-10 days old, and were kept on water pads only for 24 hrs. prior to testing. *Ae. aegypti* used in a given test session were all loaded into K&D modules at one time, with five adult females/cell, and tested within I-2 hrs.

K&D modules containing five adult females/cell were placed over a Teflon separator atop each reservoir; the sliding floors opened allowing access to the treated organdy cloth and membrane-covered cell, and the number of mosquitoes biting (proboscis inserted through the cloth) and/or observed to be engorged within each cell at the end of a 3-5 min. exposure period was recorded. Mosquitoes were used only once in a test, and then frozen and discarded.

Only tests in which three or more females fed in the control cell were analyzed, as lower feeding rates are indicative of substandard feeding readiness of that group of mosquitoes.

Feeding/probing responses observed on control, standard, and experimental compound-treated cells were compared using an R-code statistical analysis (Chauhan, K. R., et al., Journal of Medical Entomology, 42: 643-646 (2005)).

Flight Tunnel Mosquito Bioassay: The assay system consists of a six well reservoir placed at the upwind end of a flight tunnel (25 mm×60 mm×60 mm). Temperature and humidity of the flight tunnel were maintained at rearing conditions as described above. Air was constantly pushed through the flight tunnel at a wind speed of 35 ft/min. The four center wells of the six well reservoir were utilized in these bioassays. One of the 3 cm×4 cm wells contained 6 ml of citrate-phosphate-dextrose-adenine (CPDA) solution and three wells contained 6 ml of CPDA solution supplemented with adenosine triphosphate (ATP) (Sigma Chemical Co., St. Louis, Mo.). A constant-temperature water circulator warmed the reservoir to 38° C. A collagen membrane (Devro, Sandy Run, S.C.) was placed over the wells and secured to the reservoir with a light coat of high-vacuum grease (Dow Corning Corp., Midland, Mich.). The membranes were replaced after each replicate observation and additional substrate was added as needed. The reservoir and CPDA solution was used for one replicate.

Twenty mosquitoes were aspirated into a cylindrical release canister (20.5 mm×7 mm) containing a mesh screen on one end and a damper on the opposite end (Precision Plastics, Inc., Beltsville, Md.). Mosquitoes were allowed to acclimate in the canister for ten minutes and then were utilized in bioassays. The canister was placed downwind of the reservoir in the flight tunnel. Human breath was introduced in a plume into the tunnel for one minute prior to opening of the release canister. Mosquitoes were then released into the flight tunnel where the number of mosquitoes biting (proboscis inserted through the membrane) within each cell during the 10-min exposure was recorded. The solution in each well consisted of either CPDA in deionized water or one of the three experimental solutions, $10^{-2}$ M, $10^{-3}$ M, or $10^{-4}$ M ATP with CPDA, each marked with a randomly assigned food dye color (Betty Crocker). The position of each colored solution in the reservoir was also randomized. Mosquitoes were used once in a test and then aspirated for determination of engorgement. Several attractant candidates were compared one on one with each other, and with $CO_2$ in the flight tunnel to evaluate efficacy.

Attract and Kill Bait Evaluation: The assay system consists of a 1L plastic bucket covered with screened lid. A divider was placed to separate attract and kill bait from the control feeding. 50 Adult mosquitoes used in tests were between 5-10 days old, and were kept on water pads only for 24 hrs. prior to testing. Ae. aegypti used in each test session were all loaded into plastic bucket with attract and kill bait and control feeding formulation made with agarose gel containing sugar and color. In the preliminary semi-field trial, baits were charged with attractant candidates and deployed in to the either hut or tents. In one experiment 30 adult female Aedes aegypti mosquitoes were released, while in another trial at different location 20 adult female Aedes aegypti mosquitoes were released and observed for the attraction or attract-kill effect of the candidates. To incorporate invented field stable and long lasting attractants in the baits various putative devices were constructed and few of these attract and kill bait formulations were evaluated in the insectary and semi-field conditions.

Data analysis: Attraction assay data were analyzed using the Wilcoxon two-sample test (PROC NPAR1WAY, SAS 1999) to examine the difference between the numbers of mosquitoes in control from treated baits. For each chemical, knockdown and mortality at each treatment concentration were compared and separated using Tukey's honestly significant difference (HSD) test at P=0.05 (SAS/STAT Software, SAS Online Doc, Version 8, CD-ROM. SAS Institute, Inc., Cary, N.C. (1999). Means±SE of untransformed data are reported.

Results and Discussion: Highthrouhput feeding assay in twenty replicates revealed surprising attraction of test compounds at different concentration. Table 1 summarizes the in vitro results of Okoumal (1) at four different concentrations, showing consistent feeding on par with either control or better when exposed to Aedes aegypti females. Based on the chemistry and non-volatile/semi-volatile nature of commercially available, fragrance binding cyclic acetal (Givaudan), we identified a few more compounds from the literature to understand structural features of the mosquito feeding attraction.

Figure 2:
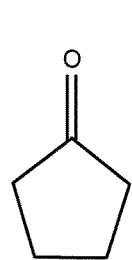
FIG. 2 shows the chemical structure of synthesized candidate attractants as described below.
Figure 2:
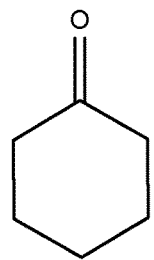
Figure 2:
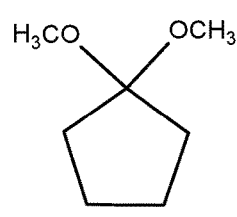
Figure 2:
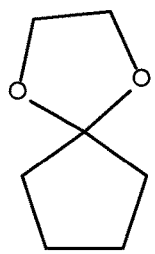
Figure 2:
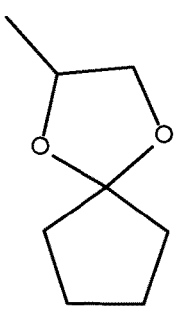
Figure 2:
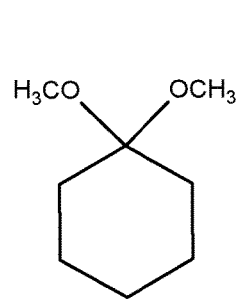
Figure 2:
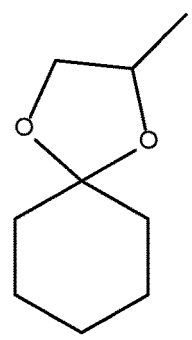

Tauxe et al. (Tauxe, G. M., et al., Cell, 155(6): 1365-1379 (2013)) described the role of a class of olfactory receptor neurons (ORNs) in female mosquitoes to detect plumes of exhaled $CO_2$ and identified several volatile chemicals as agonist to ORNs. When we evaluated one of these active ligand cyclopentanone in our flight tunnel against host seeking female mosquitoes and compared its efficacy with $CO_2$ and Okoumal, we surprisingly found consistent feeding (host seeking) preference in Okoumal (Table 2, highlighted parts). To evaluate structural features of Okoumal feeding attraction properties, we synthesized acetals, cyclic acetals, hemiacetals of ketones, aldehydes, and selected some of the commercially available sesquiterpenes acetals (FIG. 1 and FIG. 2). The general scaffolds of protected aldehydes and ketones are presented as # 3, 4 and 5 in FIG. 1. Volatile feeding attractants like cyclopentanone and cyclohexanone were converted to their ketals and cyclic ketals so that vapor pressure of these novel candidates was reduced and they can become long lasting in field conditions. Compounds I-90, I-95, I-96, I-152, and I-182 (FIG. 2) were thus synthesized by standard chemical methods for protecting carboxyl groups, where dry alcoholic (methanol, ethanol) solution of the carboxyl compound is stirred at acidic pH or a solution of carboxylic compound in benzene or toluene is azeotropically refluxed with I-2 dihydroxy ethane or I-3 dihydroxy propane.

When evaluated for host seeking preference in the flight tunnel, all these synthesized ketals surprisingly exhibited either equal or better feeding preference (Table 3) to 6-8 days old female Aedes aegypti. Cyclic ketals of cyclopentanone (I-90) and cyclohexanone (I-96) exhibited consistent feeding attraction at three different concentrations like Okoumal.

Okoumal and I-90 were also screened in semi-field conditions where 20-30 mosquitoes were released into huts to show excellent trapping (>70%). When sugar gel containing pyriproxyfen (toxicant) was spiked with 5 ml of Okoumal, 90% of the mosquitoes present in the bucket surprisingly preferred feeding to Okoumal treated gel compared to the control sugar gel. Visual host seeking cues were designed to formulate prototype attract and kill bait with invented attractant, strings soaked with sugar/molasses and reduced risk public health insecticides like boric acid or permethrin.

In field studies, Okoumal (1) was evaluated as an attractant for host seeking Aedes albopictus females in the BG Sentinel traps placed in different areas (yards). In the before and after control intervention evaluation, one standard BG Sentinel mosquito trap was placed in each of the 10 yards and mosquitoes were trapped for 24 hr periods in ten replicates. The first five replicates were before adding Okoumal attractant as intervention. The second set of five replicates included additional lure to the BG Sentinel trap. The traps with attractant lures collected more mean mosquitoes per trap per day (6-7 vs 3-4 mosquitoes), compared to control.

In the second field study different concentrations (0 to 1%) of Okoumal (1) were added to oviposition cups. Oviposition cups were placed in forested area that has known populations of Aedes albopictus, Ae. triseratus, and Ae. japonicus. Ovicups were retrieved after 10 days and accessed for the presence of mosquito eggs of different species. There was a significant effect of Okoumal concentration on numbers of oviposited eggs. Ovicups with optimal concentration had significantly higher egg numbers.

Thus attract and kill baits have been developed utilizing mosquito host-seeking stimulants that are field stable, potentially safe, pleasant, and affordable for use in a new generation of mosquito control strategies worldwide.

All of the references cited herein, including U.S. Patents and U.S. Patent Application Publications, are incorporated by reference in their entirety.

Thus, in view of the above, there is described (in part) the following: A composition which contains a compound of formula 1. A composition which does not contain a compound of formula 1. A composition which contains a compound of formula 2. A composition which does not contain a compound of formula 2. A composition which contains a compound of formula 3. A composition which does not contain a compound of formula 3. A composition which contains a compound of formula 4. A composition which does not contain a compound of formula 4. A composition which contains a compound of formula 5. A composition which does not contain a compound of formula 5. A composition which contains compound I-152. A composition which does not contain compound I-152. A composition which contains compound I-90. A composition which does not contain compound I-90. A composition which contains compound I-95. A composition which does not contain compound I-95. A composition which contains compound I-182. A composition which does not contain compound I-182. A composition which contains compound I-96. A composition which does not contain compound I-96. A composition which contains cyclohexanone. A composition which does not contain cyclohexanone.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

The invention illustratively disclosed herein suitably may be practiced in the absence of any element (e.g., method (or process) steps or composition components) which is not specifically disclosed herein. Thus the specification includes disclosure by silence ("Negative Limitations In Patent Claims," AIPLA Quarterly Journal, Tom Brody, 41(1): 46-47 (2013):

- Written support for a negative limitation may also be argued through the absence of the excluded element in the specification, known as disclosure by silence...
- Silence in the specification may be used to establish written description support for a negative limitation. As an example, in *Ex parte Lin* [No. 2009-0486, at 2,6 (B.P.A.I. May 7, 2009)] the negative limitation was added by amendment . ... In other words, the inventor argued an example that passively complied with the requirements of the negative limitation...was sufficient to provide support . . .
- This case shows that written description support for a negative limitation can be found by one or more disclosures of an embodiment that obeys what is required by the negative limitation . . . .

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Responses of female *Aedes aegypti* in the K&D module.
Feeding assay to four concentrations of Okoumal (1)

|  | mean | | Std. error | |
| --- | --- | --- | --- | --- |
| treatment | probed | fed | probed | fed |
| Ethanol | 2.5 | 2.6 | 0.39 | 0.48 |
| Deet | 0.1 | 0.1 | 0.1 | 0.1 |
| 5% Okoumal | 2.9 | 2.8 | 0.38 | 0.44 |
| 1% Okoumal | 3.9 | 3.5 | 0.21 | 0.31 |
| 0.25% Okoumal | 3 | 2.8 | 0.3 | 0.37 |
| 0.1% Okoumal | 3.3 | 3.6 | 0.38 | 0.33 |

TABLE 2

Preference of female *Aedes aegypti* in the Flight tunnel to $CO_2$, cyclopentanone, and Okoumal (1)

|  | mean | | Std. error | |
| --- | --- | --- | --- | --- |
| treatment | probed | fed | probed | fed |
| air | 0.1 | 0.1 | 0.1 | 0 |
| CO2 (dry ice) + air | 2.1 | 1.8 | 0.19 | 0.22 |
| CO2 (dry ice) + air | 2.2 | 2 | 0.3 | 0.25 |
| 1% Okoumal | 4.1 | 3.8 | 0.21 | 0.18 |
| CO2 (dry ice) + air | 2.3 | 2.1 | 0.1 | 0 |
| 1% cyclopentanone | 2.8 | 2.1 | 0.38 | 0.2 |
| CO2 (dry ice) + air | 3.7 | 3 | 0.3 | 0.13 |
| 0.1% Okoumal | 3.6 | 3.9 | 0.19 | 0.06 |
| CO2 (dry ice) + air | 3.1 | 2.8 | 0.11 | 0.02 |
| 0.1% cyclopentanone | 2.2 | 2.6 | 0.2 | 0.12 |

TABLE 3

Preference of female Aedes aegypti in the Flight tunnel to synthetic candidates (mean of triplicates)

|  | 0.10% | | 1.00% | | 5% | |
| --- | --- | --- | --- | --- | --- | --- |
| treatment | probed | fed | probed | fed | probed | fed |
| control | 5.7 | 2.3 | 3.3 | 1 | 1 | 0.7 |
| cyclopentanone | 7 | 3 | 5.7 | 2 | 1.7 | 1 |
| control |  |  | 0.1 | 0 | 1.7 | 0.3 |
| cyclohexanone |  |  | 0.7 | 0.3 | 3.7 | 1.7 |
| control | 4 | 1 | 3.3 | 1 | 1.7 | 1 |
| Okoumal | 18.3 | 3.3 | 9.7 | 2.8 | 13.3 | 2.3 |
| control | 3.3 | 0.3 | 4 | 2.3 | 8 | 2 |
| I-90 | 5.7 | 2.7 | 8.3 | 4 | 8.7 | 3 |
| control |  |  | 7.7 | 0.3 | 7.7 | 2.3 |
| I-95 |  |  | 12 | 3.3 | 8.3 | 3.3 |
| control | 2.3 | 0.3 | 5 | 2 | 6.7 | 2 |
| I-96 | 6.3 | 3 | 8.3 | 2.7 | 12.7 | 2.7 |
| control |  |  | 1.7 | 0.3 | 1.7 | 1.3 |
| I-152 |  |  | 1.3 | 0.7 | 1.7 | 1 |
| control |  |  | 5 | 2.3 | 7.3 | 2 |
| I-182 |  |  | 5.7 | 2.7 | 12.3 | 2 |

I claim:

1. An insect attracting composition comprising at least two compounds of formula 1, 2, 3, 4 and 5:

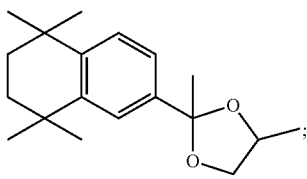

1

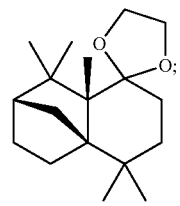

2

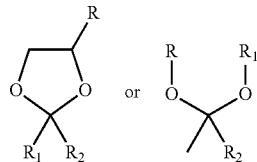

3 where R, R₁, and R₂ are H, n-alkanes, alkanes, cycloalkanes, or aryl; where n-alkanes are $(CH_2)_nH$ where n is 1 to 8, alkanes are branched-$(CH_2)_nH$ where n is 1 to 8; cycloalkanes are cyclobutane, cyclopentane, cyclohexane, or cycloheptane, aryl is benzene or alkyl benzene where alkyl is C1-6 alkyl;

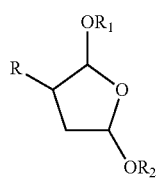

4 where R, R₁, and R₂ are H, n-alkanes, alkanes, cycloalkanes, or aryl; n-alkanes are —$(CH_2)_nH$ where n is 1 to 8, alkanes are branched-$(CH_2)_nH$ where n is 1 to 8; cycloalkanes are cyclobutane, cyclopentane, cyclohexane, or cycloheptane, aryl is benzene and or alkyl benzene where alkyl is C1-6 alkyl;

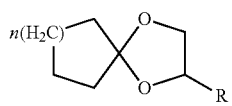

5 where R is H, n-alkanes, alkanes, cycloalkanes, or aryl and n: 1 to 8; n-alkanes are —$(CH_2)_nH$ where n is 1 to 8, alkanes are branched-$(CH_2)_nH$ where n is 1 to 8; cycloalkanes are cyclobutane, cyclopentane, cyclohexane, or cycloheptane, aryl is benzene or alkyl benzene where alkyl is C1-6 alkyl;

and optionally a carrier or carrier material.

2. A method of attracting insects, said method comprising treating an object or area with an insect attracting effective amount of an insect attracting composition comprising at least two compounds of formula 1, 2, 3, 4 and 5:

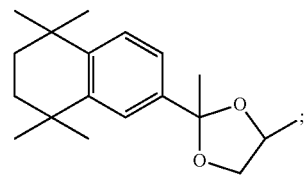

1

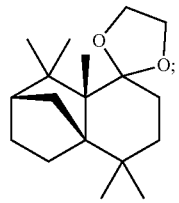

2

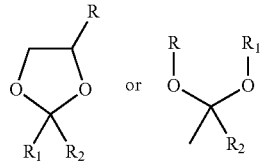

3 where R, R₁, and R₂ are H, n-alkanes, alkanes, cycloalkanes, or aryl; where n-alkanes are $(CH_2)_nH$ where n is 1 to 8, alkanes are branched-$(CH_2)_nH$ where n is 1 to 8; cycloalkanes are cyclobutane, cyclopentane, cyclohexane, or cycloheptane, and aryl is benzene or alkyl benzene where alkyl is C1-6 alkyl;

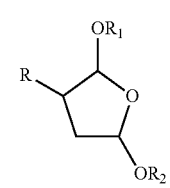

4 where R, R₁, and R₂ are H, n-alkanes, alkanes, cycloalkanes, or aryl; n-alkanes are —$(CH_2)_nH$ where n is 1 to 8, alkanes are branched-$(CH_2)_nH$ where n is 1 to 8; cycloalkanes are cyclobutane, cyclopentane, cyclohexane, or cycloheptane, and aryl is benzene or alkyl benzene where alkyl is C1-6 alkyl;

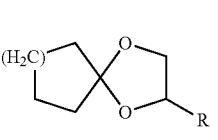

5 where R is H, n-alkanes, alkanes, cycloalkanes, or aryl and n: 1 to 8; n-alkanes are —$(CH_2)_nH$ where n is 1 to 8, alkanes are branched-$(CH_2)_nH$ where n is 1 to 8; cycloalkanes are cyclobutane, cyclopentane, cyclohexane, or cycloheptane, and aryl is benzene or alkyl benzene where alkyl is C1-6 alkyl;

and optionally a carrier or carrier material.

* * * * *